(12) United States Patent
Fundingsland et al.

(10) Patent No.: US 6,971,874 B2
(45) Date of Patent: Dec. 6, 2005

(54) DENTAL RESTORATIVE FORMULA SELECTOR AND METHODS OF USE

(75) Inventors: Jon W. Fundingsland, Stillwater, MN (US); Dawn H. McArthur, Woodbury, MN (US); Renee N. Nord, Apple Valley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 216 days.

(21) Appl. No.: 10/272,488

(22) Filed: Oct. 16, 2002

(65) Prior Publication Data

US 2004/0076920 A1 Apr. 22, 2004

(51) Int. Cl.[7] ............................................. A61C 19/10
(52) U.S. Cl. ..................................... 433/26; 433/203.1
(58) Field of Search ................................ 433/26, 203.1; 356/408; 264/20

(56) References Cited

U.S. PATENT DOCUMENTS

| | | | |
|---|---|---|---|
| 4,828,117 A * | 5/1989 | Panzera et al. | ............ 206/63.5 |
| 5,189,285 A | 2/1993 | Young, Jr. | |
| 5,261,815 A | 11/1993 | Pozzi | |
| 5,716,050 A | 2/1998 | Jagosz | |
| 5,731,572 A | 3/1998 | Winn | |
| 5,989,022 A | 11/1999 | Yamamoto et al. | |
| 6,031,172 A | 2/2000 | Papadopoulos | |
| 6,167,627 B1 | 1/2001 | Wilder et al. | |
| 6,315,554 B1 | 11/2001 | Coste et al. | |
| 6,315,566 B1 | 11/2001 | Shen et al. | |
| 6,323,410 B1 | 11/2001 | Rackow | |
| 6,330,970 B1 | 12/2001 | Whalen | |
| 6,354,835 B1 | 3/2002 | Maini | |
| 6,393,707 B1 | 5/2002 | Maffei | |
| 2001/0049082 A1 | 12/2001 | Kerschbaumer et al. | |
| 2002/0064751 A1 | 5/2002 | Lehmann | |

OTHER PUBLICATIONS

3M Technical Product Profile, "Filtek™ 110 Anterior Restorative,"3M Dental Products, St. Paul, MN, 28 pgs. total, no month indicated, 2000.

* cited by examiner

Primary Examiner—John J Wilson
(74) Attorney, Agent, or Firm—Sean Edman (57) ABSTRACT

A dental restorative formula selector including a formula matrix is disclosed. The formula matrix includes tooth shade markings and two or more dental restorative formulas correlated to each tooth shade marking. Each dental restorative formula includes at least one dental restorative composition code, and at least one dental restorative formula of the two or more dental restorative formulas provided includes at least two dental restorative composition codes. The dental restorative formula selector may provide a practitioner with multiple dental restorative formula options for restoring teeth using dental restorative compositions.

15 Claims, 6 Drawing Sheets

DENTAL RESTORATIVE FORMULA SELECTOR AND METHODS OF USE

FIELD OF INVENTION

The present invention relates generally to dental restoratives. More particularly, the invention relates to a dental restorative formula selector for use in preparing a dental restorative and methods of using the same.

BACKGROUND

Dental restoratives include, for example, bridges, inlays, onlays, veneers, filling materials, composite materials, entire artificial teeth, etc. To repair or replace a damaged tooth, it is desirable to match the restored or replacement tooth to approximate the original tooth's color or shade characteristics.

Practitioners typically use a shade guide to aid in matching the dental restorative to the patient's existing teeth. In general, a shade guide includes a number of tabs, teeth, or other indicia that each show a different shade. The shade guide may, in some instances, provide a dental restorative formula for matching a particular shade. The practitioner then prepares the dental restorative of the given shade using the provided dental restorative formula and applies the dental restorative according to techniques known in the art.

New dental composite systems for preparing dental restoratives are often created with a layering technique in mind. It has been found that teeth tend to have varying shades, translucency, and opacity through their structures. To approximate these variances, practitioners may layer several dental restorative compositions of varying shades to provide a more natural looking dental restorative that blends well with the patient's existing teeth. When utilizing the layering technique, different body, dentin, enamel, and incisal shades and opacities might be used. However, when presented with a system of thirty or more different shades and opacity options, the practitioner needs guidance as to which shades are most appropriate and which dental restorative compositions to use.

Further, not all dentists are willing to perform this multi-layering technique, particularly if the technique requires the use, e.g., of three or more different dental restorative compositions. In addition, not all restorations are of a size and/or location that require a multi-layer approach.

SUMMARY OF THE INVENTION

The present invention provides a dental restorative formula selector including a formula matrix. The dental restorative formula selector provides multiple options for a practitioner to prepare dental restoratives of different shades and opacities. A practitioner, using the dental restorative formula selectors of the present invention, is able to choose from two or more dental restorative formulas correlated to each tooth shade for application to at least one tooth of a patient's teeth. At least one of the dental restorative formulas provided to the practitioner for a selected tooth shade includes two or more dental restorative composition codes. The practitioner may then select the relative complexity of the formula to be used. In other instances, if the practitioner does not have one or more dental restorative compositions required by a multi-composition dental restorative formula, then the practitioner may choose a less complex formula for the selected tooth shade.

As used herein, a "dental restorative composition" is defined as a composition that may be used to prepare a dental restorative.

As used herein, a "dental restorative composition code" is an alpha-numeric code or any other indicia representative of a dental restorative composition.

As used herein, a "dental restorative formula" is a sequence or recipe for preparing a dental restorative. The dental restorative formulas of the present invention may include one or more dental restorative composition codes.

In one aspect, the present invention provides a method of identifying a dental restorative formula. The method includes selecting a tooth shade and providing two or more dental restorative formulas correlated to the tooth shade. Each formula of the two or more dental restorative formulas includes at least one dental restorative composition code, and at least one dental restorative formula of the two or more dental restorative formulas includes at least two dental restorative composition codes. The method further includes selecting one dental restorative formula from the two or more dental restorative formulas as a selected dental restorative formula.

In another aspect, the present invention provides a method of identifying a dental restorative formula, including selecting a tooth shade, and providing a dental restorative formula selector including a formula matrix on a first major surface of a medium. The formula matrix includes a plurality of tooth shade markings and a plurality of dental restorative formulas. Two or more dental restorative formulas of the plurality of dental restorative formulas are correlated to each tooth shade marking of the plurality of tooth shade markings. The method further includes providing two or more dental restorative formulas correlated to the tooth shade using the dental restorative formula selector. Each formula of the two or more dental restorative formulas includes at least one dental restorative composition code, and at least one dental restorative formula of the two or more dental restorative formulas comprises at least two dental restorative composition codes. The method further includes selecting one dental restorative formula from the two or more dental restorative formulas as a selected dental restorative formula.

In another aspect, the present invention provides a dental restorative formula selector. The dental restorative formula selector includes a medium including a first major surface and a formula matrix on the first major surface of the medium. The formula matrix includes a plurality of tooth shade markings and a plurality of dental restorative formulas. Two or more dental restorative formulas of the plurality of dental restorative formulas are correlated to each tooth shade marking of the plurality of tooth shade markings. Further, each dental restorative formula of the plurality of dental restorative formulas includes at least one dental restorative composition code, and at least one dental restorative formula of the two or more dental restorative formulas correlated to each tooth shade marking includes at least two dental restorative composition codes.

In another aspect, the present invention provides a dental restorative kit, including a dental restorative formula selector. The selector includes a medium including a first major surface and a formula matrix on the first major surface of the medium. The formula matrix includes a plurality of tooth shade markings and a plurality of dental restorative formulas. Two or more dental restorative formulas of the plurality of dental restorative formulas are correlated to each tooth shade marking of the plurality of tooth shade markings. Further, each formula of the plurality of dental restorative formulas includes at least one dental restorative composition code, and at least one dental restorative formula of the two or more dental restorative formulas includes at least two dental restorative composition codes. The dental restorative kit further includes at least one dental restorative composition.

In another aspect, the present invention provides a dental restorative formula selector computer system, including a display and a memory device. A formula matrix is stored in the memory device. The formula matrix includes a plurality of tooth shade markings and a plurality of dental restorative formulas. Two or more dental restorative formulas of the plurality of dental restorative formulas are correlated to each tooth shade marking of the plurality of tooth shade markings. The computer system further includes a controller in communication with the memory device and the display. The controller is operable to receive a selected tooth shade input, compare the selected tooth shade input to the formula matrix stored in the memory, and provide the two or more dental restorative formulas correlated to the selected tooth shade input using the formula matrix. Each dental restorative formula of the plurality of dental restorative formulas includes at least one dental restorative composition code. Further, at least one dental restorative formula of the two or more dental restorative formulas correlated to each tooth shade marking includes at least two dental restorative composition codes. The controller is further operable to display the two or more dental restorative formulas on the display.

DETAILED DESCRIPTION OF ILLUSTRATIVE EMBODIMENTS OF THE INVENTION

In the following detailed description of the embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention.

The present invention shall be generally described with reference to one exemplary embodiment depicted in FIG. 1. Thereafter, various alternative embodiments and examples of the present invention shall be described with reference to FIGS. 2–7.

While the present invention has application to any type of dental restorative or restorative technique, it may be used with dental restorative compositions such as those marketed by 3M Company, St. Paul, Minn.

Figure 1:
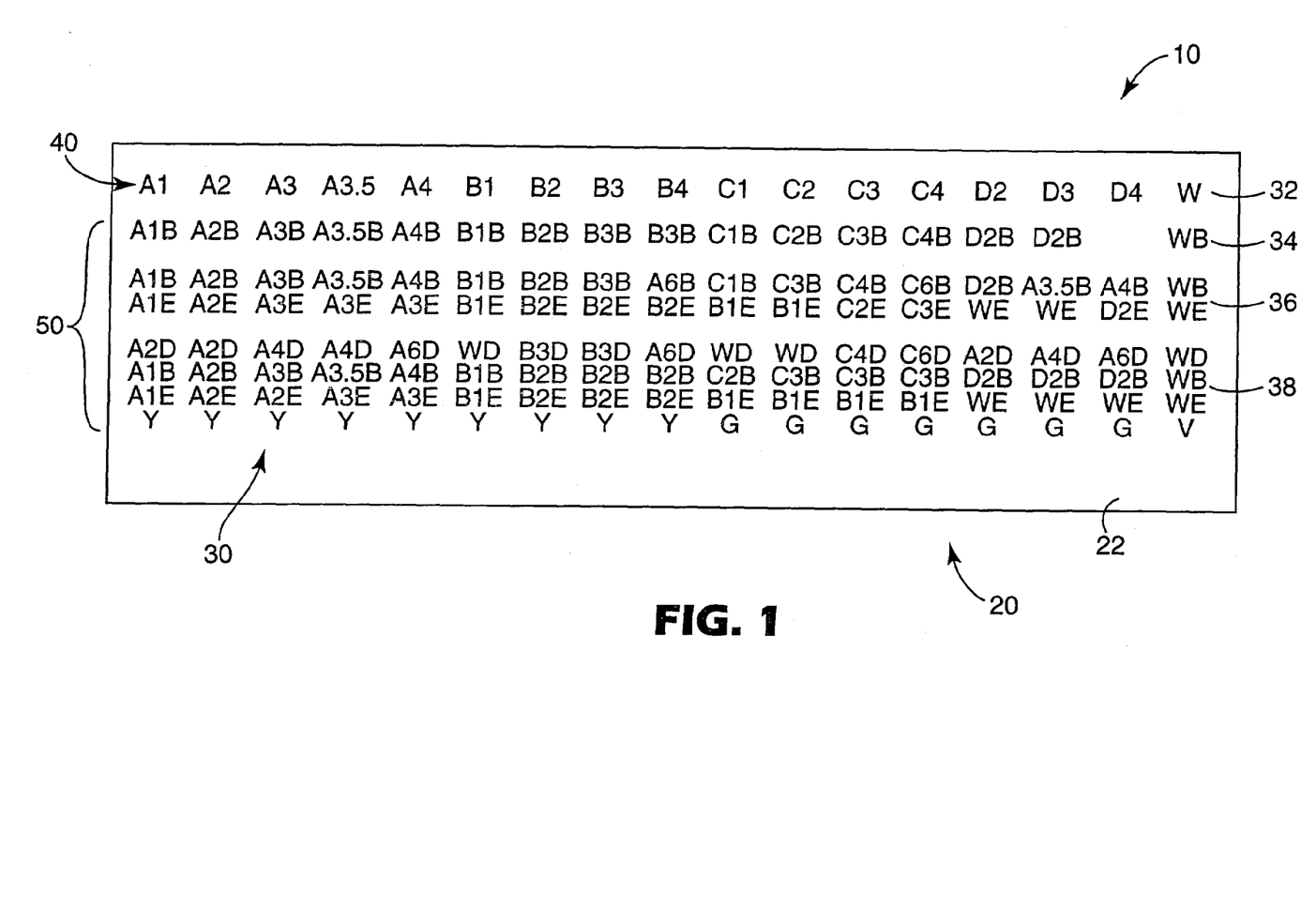
FIG. 1 is a diagram of one dental restorative formula selector according to the present invention.

FIG. 1 shows an illustrative dental restorative formula selector 10 according to the present invention. The dental restorative formula selector 10 provides multiple options for preparing a dental restorative for each tooth shade that approximates the shade of a patient's teeth. The different options may preferably vary in complexity, thereby providing a practitioner with the opportunity to select a dental restorative formula that best suits the patient and the practitioner's talent.

The dental restorative formula selector 10 may be presented on a medium 20. The medium 20 may be any material known in the art for presenting markings or information to be viewed, e.g., paper, polymeric material, computer display, etc. Although depicted as rectilinear, the medium 20 may be any suitable shape, e.g., circular, three-dimensional, etc.

The depicted medium 20 includes a first major surface 22. On the first major surface 22 of the medium 20 is a formula matrix 30. The formula matrix 30 includes tooth shade markings 40 and dental restorative formulas 50. The tooth shade markings 40, which are provided in row 32 of formula matrix 30, may, e.g., correspond to tooth shades on a shade guide. As used herein, the term "formula matrix" may include any collection of information or data that is organized in a way that aids a practitioner in selecting from dental restorative formulas correlated to different tooth shades for preparing dental restoratives.

As used herein, a "shade guide" is defined as a guide for determining the color and opacity of a patient's teeth. A typical shade guide may include, e.g., an elongated, linear holder containing a plurality of specimens. Each specimen has a predetermined shade and hue for matching with the patient's natural teeth. Examples of shade guides are the VITAPAN classical shade guide manufactured by Vita Zahnfabrik, Germany, the VITAPAN 3D shade guide, the TETRIC CERAM shade guide manufactured by Ivoclar/Vivadent, Germany, the ESTHETX shade guide manufactured by Dentsply/Caulk, USA, and the FILTEK Z250 Universal Restorative shade guide manufactured by 3M ESPE, USA.

The dental restorative formulas 50 preferably include several different types of dental restorative formulas correlated to each tooth shade marking 40. For example, row 34 of the formula matrix 30 includes single composition dental restorative formulas for each of the tooth shade markings 40. In general, a single composition dental restorative formula is a formula including only one dental restorative composition code to match the selected tooth shade. For example, to match tooth shade marking "A3" using a single composition formula, the embodiment illustrated in FIG. 1 provides the formula A3B. To implement the single composition formula, a practitioner would then use only the dental restorative composition that is correlated to the dental restorative composition code "A3B."

The formula matrix 30 also includes two-composition dental restorative formulas, which are provided in row 36. For example, to match the tooth shade B4, the formula matrix illustrated in FIG. 1 would provide a two-composition formula of A6D+B2E. To implement this formula, a practitioner would first apply a layer of a dental restorative composition correlated to the dental restorative composition code "A6D." The practitioner would then apply a layer of dental restorative composition correlated to the dental restorative composition code "B2E" over at least a portion of the layer of dental restorative composition correlated to "A6D."

Further, the formula matrix 30 includes multi-composition dental restorative formulas in row 38. Each multi-composition dental restorative formula includes at least three dental restorative composition codes that are applied by the practitioner in layers. For example, to produce a restorative having a tooth shade of A2, the formula matrix 30 provides a multi-composition formula of A2D+A2B+A2E+Y for the embodiment illustrated in FIG. 1.

In the embodiment depicted in FIG. 1, each tooth shade marking 40 is correlated to three dental restorative formulas 50, where each dental restorative formula includes at least one dental restorative composition code, and at least one of the dental restorative formulas includes two or more dental restorative composition codes. For example, the tooth shade indicated as "A1" in formula matrix 30 correlates to the dental restorative formulas A1B, A1B+A1E, and A2D+A1B+A1E+Y. The dental restorative formula A1B includes one dental restorative composition code, the formula A1B+A1E includes two dental restorative composition codes, and the formula A2D+A1B+A1E+Y includes four dental restorative composition codes. In other words, the formula matrix 30 provides the practitioner with several options correlated to a selected tooth shade for matching a tooth shade.

Although the depicted formula matrix 30 correlates three different dental restorative formulas 50 with each tooth shade marking 40, it should be understood that other variations are possible. For example, the formula matrix 30 may correlate as few as two dental restorative formulas to each tooth shade marking. In other alternatives, four or more dental restorative formulas may be correlated to each tooth shade marking.

Although FIG. 1 does provide a formula matrix 30 having a specific correlation of tooth shades with dental restorative formulas, those skilled in the art will understand that the formula matrix 30 may be arranged in many different ways to accommodate different dental restorative compositions and tooth shade requirements.

It may be preferred that the formula matrix 30 include dental restorative formulas corresponding to each tooth shade that vary in complexity. For example, it may be preferred that the different dental restorative formulas correlated to each tooth shade include one dental restorative formula with a single dental restorative composition code, and at least another dental restorative formula that includes two or more dental restorative composition codes.

Although FIG. 1 depicts the formula matrix 30 as including the tooth shade markings and the dental restorative formulas in rows and columns, those skilled in the art will understand that the presentation of the formula matrix 30 may include any form or arrangement that provides two or more dental restorative formulas correlated to each selected tooth shade marking.

In use, the practitioner may select a tooth shade using a shade guide as is known in the art. As used herein, a tooth shade may include both a tooth's color and/or opacity. The practitioner matches the selected tooth shade with a tooth shade marking 40 of the formula matrix 30. Once the tooth shade marking 40 is selected, the formula matrix 30 provides two or more dental restorative formulas correlated to the selected tooth shade marking. In other words, the formula matrix 30 provides the practitioner with multiple options for preparing a restorative to match the selected tooth shade.

For example, to match a tooth shade of B1, the formula matrix 30 provides the practitioner with a single composition formula in row 34 (B1B), a two-composition formula in row 36 (B1B+B1E), and a multi-composition formula in row 38 (WD+B1B+B1E+Y). Although depicted as providing a single composition, a two-composition, and a multi-composition formula for each tooth shade, the formula matrix 30 may also include any number of formula options correlated with a selected tooth shade.

The practitioner would then select from the two or more dental restorative formulas provided and form the dental restorative using the selected dental restorative formula. For example, for dental restorative formulas that include two or more dental restorative composition codes, the practitioner would apply layers of dental restorative compositions corresponding to each dental restorative composition code in the appropriate sequence.

Although the formula matrix 30 illustrated in FIG. 1 includes one set of tooth shade markings 40, the formula matrix 30 may include more than one set of tooth shade markings, where each set is based upon a different shade guide, e.g., the VITAPAN classical shade guide manufactured by Vita Zahnfabrik, Germany, the TETRI CERAM shade guide manufactured by Ivoclar/Vivadent, Germany, etc.

The dental restorative formula selectors of the present invention may be presented in various forms. For example, FIGS. 2–5 illustrate a dental restorative formula selector 100 according to another embodiment of the present invention. As illustrated, dental restorative formula selector 100 includes medium 120 (as best illustrated in FIG. 4). Medium 120 is similar in many respects to medium 20 of FIG. 1. Medium 120 includes a first major surface 122 and a second major surface 123. The medium 120 also includes a perimeter 124 and a center 126. Although depicted as circular in shape, those skilled in the art will understand that medium 120 may be any suitable shape, e.g., rectangular, oval, octagonal, etc.

The medium 120 further includes a formula matrix 130 on the first major surface 122. The formula matrix 130 is similar in design to formula matrix 30 of FIG. 1. Formula matrix 130 includes tooth shade markings 140 and dental restorative formulas 150. One of the differences between formula matrix 130 and formula matrix 30 of FIG. 1 is that tooth shade markings 140 and dental restorative formulas 150 are arranged in a generally circular pattern surrounding center 126.

Formula matrix 130 is arranged such that two or more dental restorative formulas 150 are correlated to each tooth shade marking 140. For example, tooth shade marking A1 is correlated to single composition dental restorative formula A1B, two-composition dental restorative formula A1B+A1E, and multi-composition dental restorative formula A2D+A1B+A1E+Y.

Each dental restorative formula 150 of formula matrix 130 includes at least one dental restorative composition code. In addition, at least one formula of the two or more dental restorative formulas correlated to each tooth shade marking includes at least two or more dental restorative composition codes. In other words, the formula matrix 130 provides a practitioner with two or more dental restorative formulas for a selected tooth shade marking, where at least one of the two or more dental restorative formulas includes a dental restorative formula having two or more dental restorative composition codes.

Figure 2:
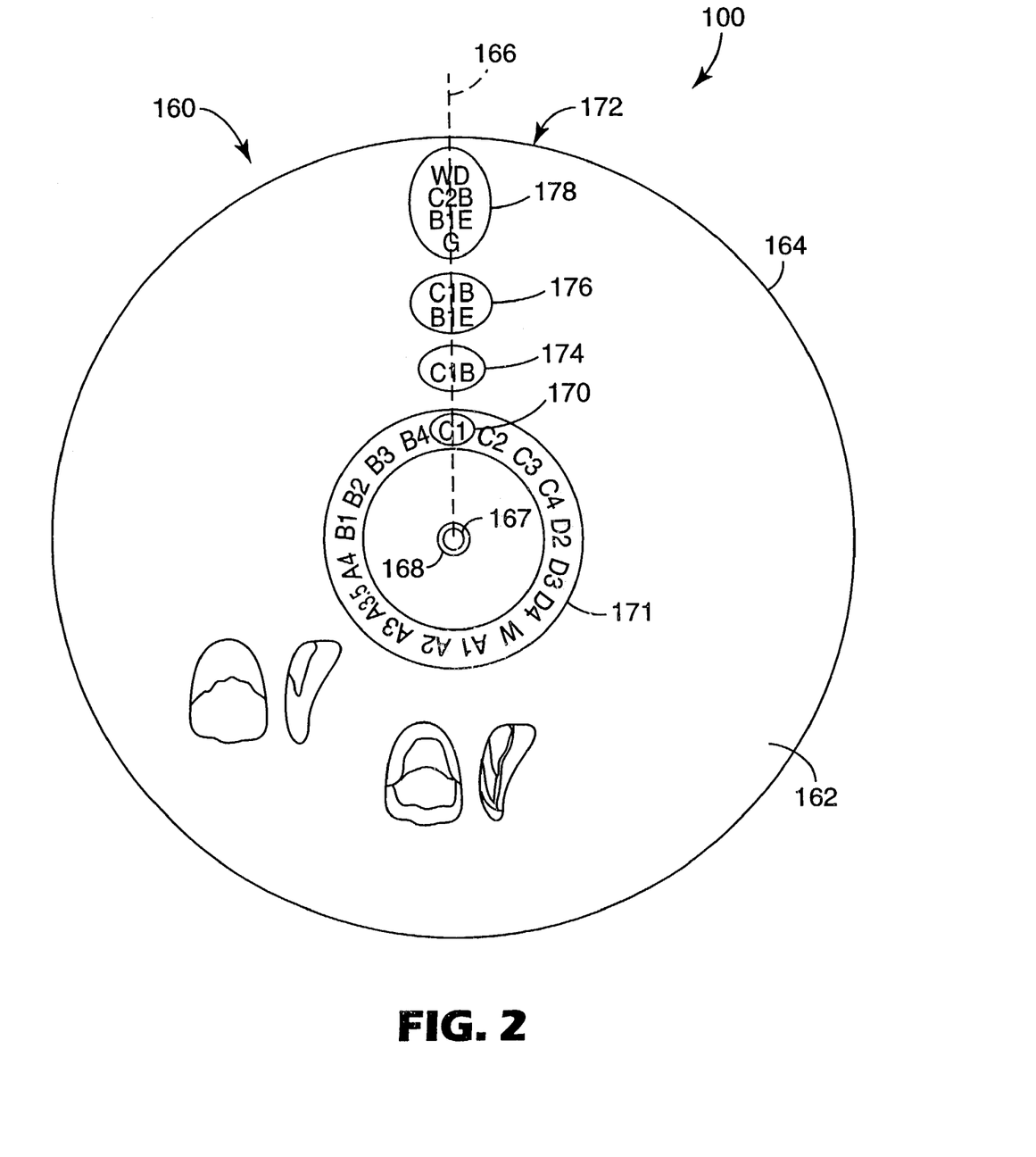
FIG. 2 is a diagram of another dental restorative formula selector including a selector element according to the present invention.
Figure 3:
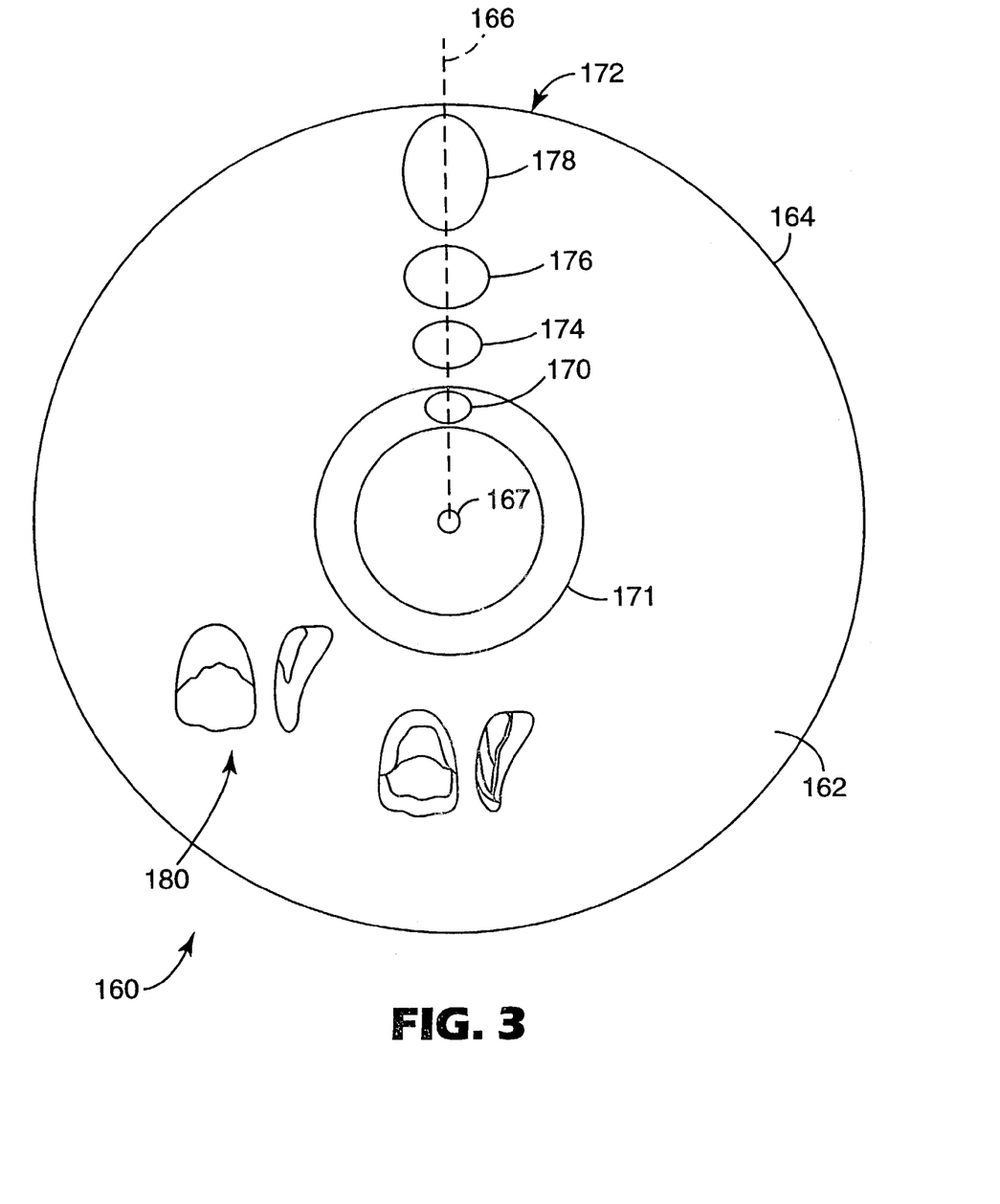
FIG. 3 is a diagram of the selector element of the dental restorative formula selector of FIG. 2.
Figure 4:
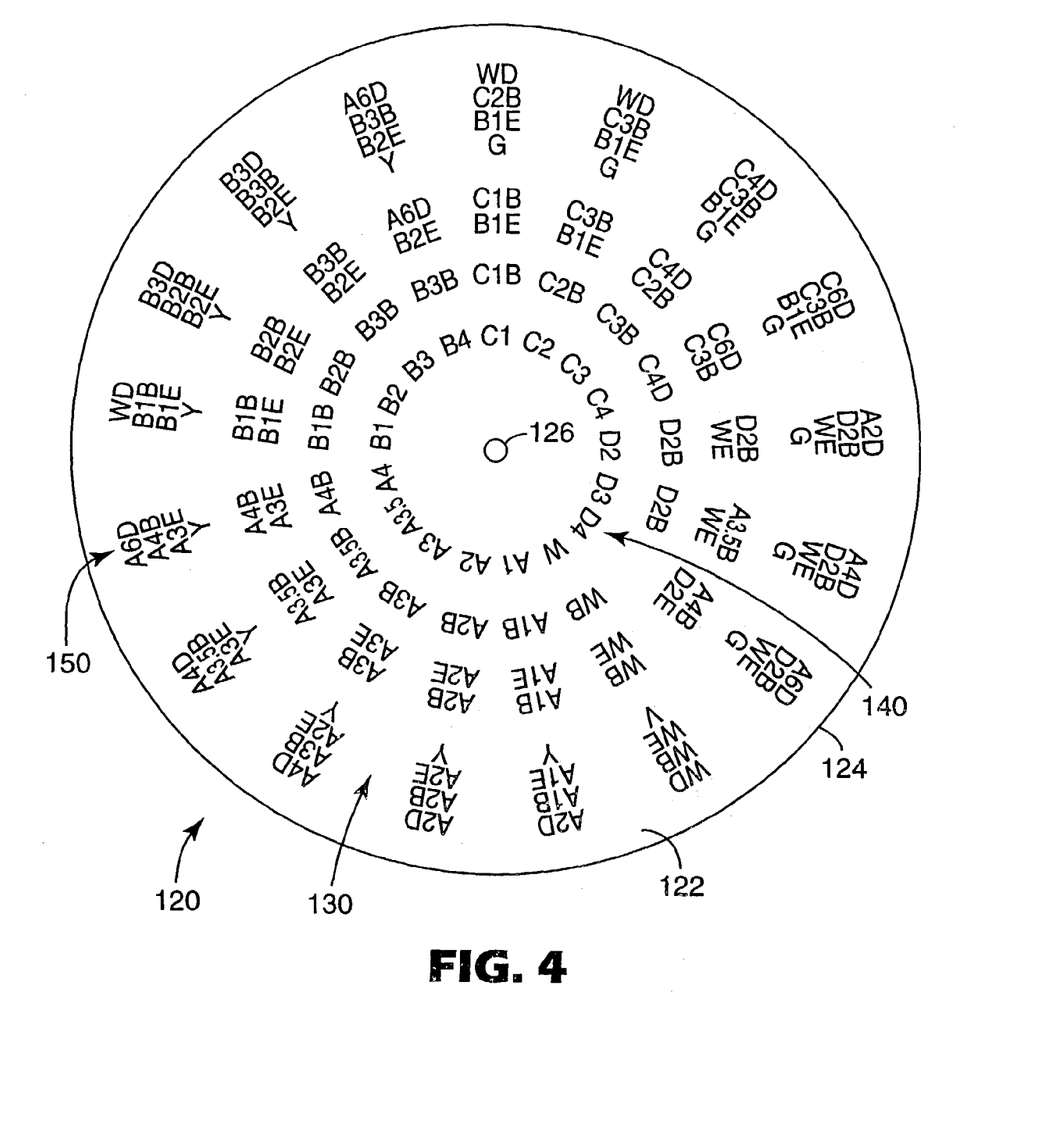
FIG. 4 is a diagram of the medium of the dental restorative formula selector of FIG. 2.

The dental restorative formula selector 100 further includes a selector element 160 (as best seen in FIGS. 2–3). The selector element 160 includes a first major surface 162, a second major surface (not shown), and a perimeter 164. The selector element 160 may be manufactured using any suitable material known in the art, e.g., paper, polymeric material, laminate, etc. Although depicted as having a circular shape, selector element 160 may include any suitable shape, e.g., rectangular, oval, octagonal, etc. It may be preferred that selector element 160 have the same or substantially similar shape to medium 120. Both the selector element 160 and the medium 120 are of a size that a practitioner may comfortably grasp and operate the dental restorative formula selector 100 as described herein. Further, although depicted as opaque, the selector element 160 may be manufactured using translucent materials such that all of the first major surface 122 of medium 120 is viewable through the first major surface 162 of the selector element 160.

The selector element 160 includes a center 167. The center 167 and perimeter 164 define radial axis 166. An input window 170 is located on the first major surface 162 of the selector element 160 proximate the center 167 along axis 166. Also located along axis 166 are three output windows 172. The three output windows 172 include a single shade window 174, a two-shade window 176, and a multi-shade window 178. The three output windows 172 may be in any order along axis 166. Further, the three output windows 172 and the input window 170 may also be located on first major surface 162 such that they do not lie along any particular axis. Although depicted as including three output windows 172, the selector element 160 may include any suitable number of output windows 172. For example, all of the different dental restorative formulas correlated to a tooth shade may be viewed in a single output window.

The second major surface of the selector element 160 is adjacent the first major surface 122 of medium 120 such that selected tooth shade markings and dental restorative formulas on the first major surface 122 of the medium 120 are viewable through the input window 170 and at least one of the three output windows 172 of the selector element 160. The selector element 160 may be rotatably connected to medium 120 using connector 168 located proximate center 167 of the selector element 160 and center 126 of medium 120. The connector 168 may be any suitable connector known in the art, e.g., rivet, snap, pin, etc.

When the second major surface of the selector element 160 is located adjacent the first major surface 122 of medium 120, the dental restorative formula selector 100 is operable such that a practitioner may move selector element 160 and medium 120 relative to each other to view a selected tooth shade marking 140 in the input window 170. If the selector element 160 is rotatably connected to medium 120, then a practitioner may rotate the selector element 160 relative to the medium 120 to select a particular tooth shade marking 140 in input window 170.

The selector element 160 is configured to be moved such that a selected tooth shade marking 140 is viewable through the input window 170, as is illustrated in FIG. 2. Further, at least one dental restorative formula 150 correlated to the selected tooth shade marking 140 is viewable through at least one output window of the three output windows 172. As illustrated in FIG. 2, tooth shade marking C1 is viewable through input window 170. Selected tooth shade C1, in the embodiment illustrated in FIG. 2, is correlated to single composition formula C1B, two-composition formula C1B+B1E, and multi-composition formula WD+C2B+B1E+G. The single composition formula is viewable through the single shade window 174, the two-composition formula is viewable through the two-shade window 176, and the multi-composition formula is viewable through the multi-shade window 178. In other words, for selected tooth shade C1, the practitioner is provided with two or more dental restorative formulas, where at least one of the two or more dental restorative formulas includes two or more dental restorative composition codes.

The selector element 160 illustrated in FIGS. 2–5 includes a clear ring 171 that allows all of the tooth shade markings 140 to be viewed simultaneously. This may allow the practitioner to more conveniently select a tooth shade marking 140 by moving the selector element 160 until the desired tooth shade marking 140 is viewed in the input window 170.

Figure 5:
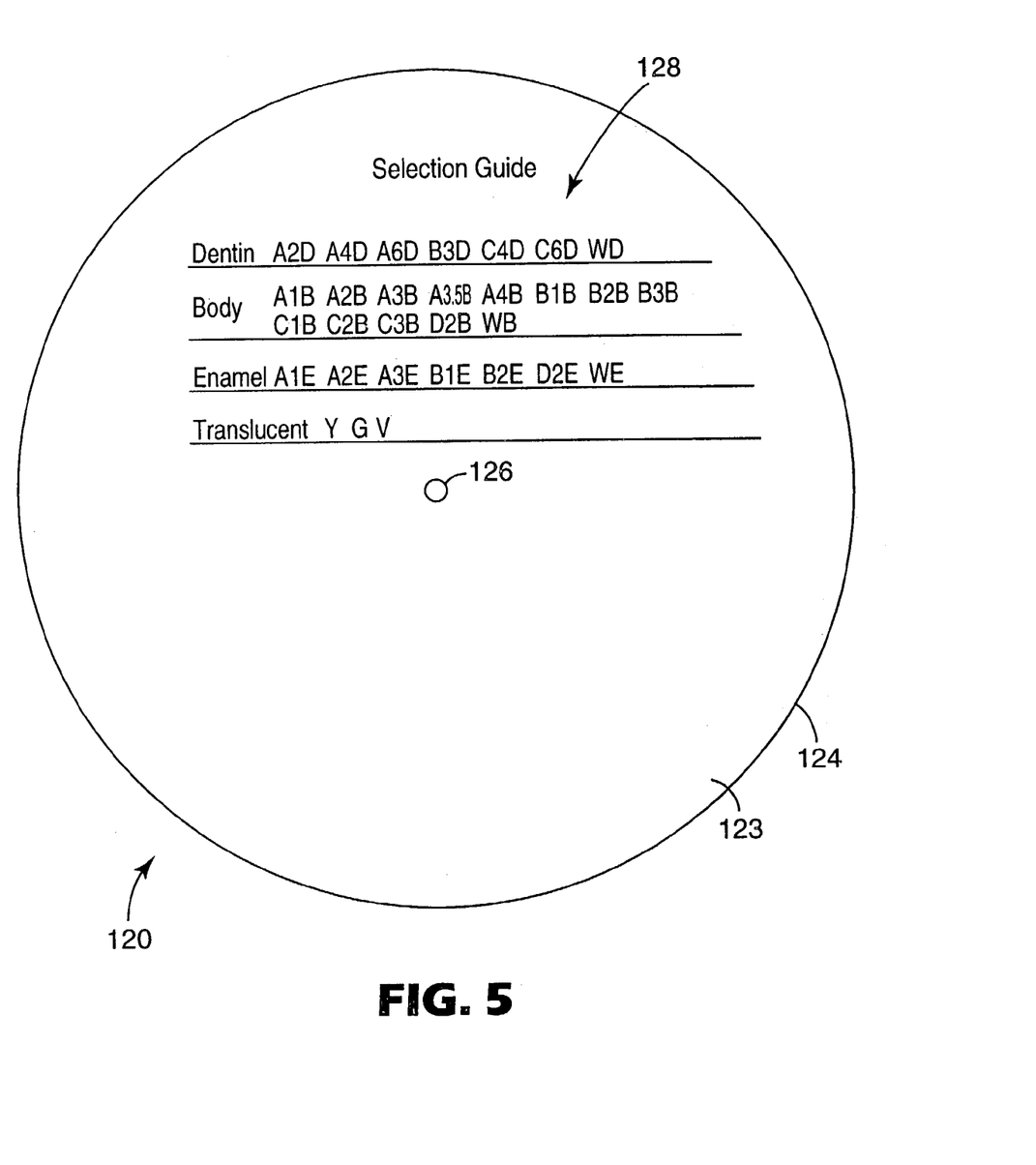
FIG. 5 is a bottom view of the dental restorative formula selector of FIG. 2.

The selector element 160 may include various indicia 180 that are placed on the first major surface 162. Such indicia 180 may include information relevant to the layering process of the dental restoratives being used. Further, the second major surface 123 of medium 120 may also include various indicia 128 (as seen in FIG. 5).

The dental restorative formula selector 100 may further be presented in any suitable shape or configuration. For example, the selector element 160 may include two separated layers where the medium is located between the two layers to form a linear slide rule configuration.

Figure 6:
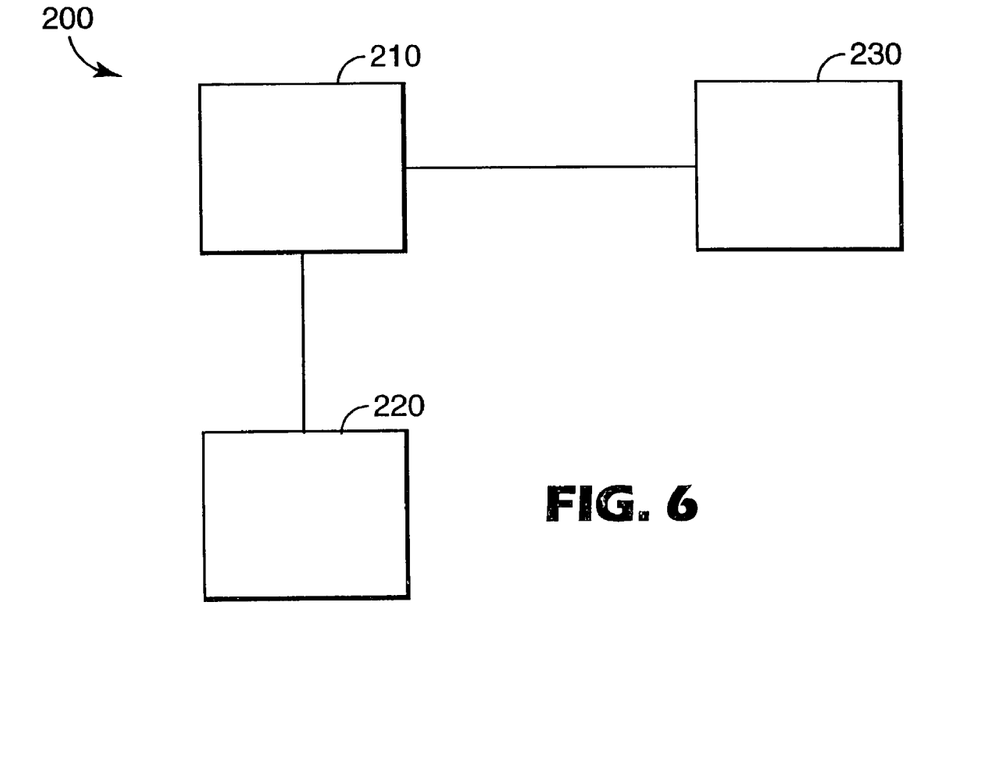
FIG. 6 is a schematic diagram of another dental restorative formula selector including a computer and display according to the present invention.

FIG. 6 illustrates a dental restorative formula selector system 200 according to another embodiment of the present invention. The system 200 may be any suitable hardware- or software-based, or a combination of hardware- and software-based system known in the art. The system 200 includes a controller 210, a display 220 in communication with the controller 210, and memory 230 also in communication with the controller 210. Stored in memory 230 is a dental restorative formula selector including a formula matrix as described herein.

The controller 210 may be any microprocessor-based computer. For example, controller 210 may be a desktop system, a website server, a personal digital assistant, etc. The display 220 may be any viewable display known in the art. For example, the display may be a typical CRT display or flat panel for a desktop computer system, or the display may include a web-based page or series of pages operable to display the dental restorative formulas described herein. Further, the memory 230 may be any suitable data storage device known in the art. For example, the memory 230 may be a drive, RAM, ROM, DVD drive, etc.

In general, the controller 210 is operable to receive a selected tooth shade input from a practitioner as is described herein. The selected tooth shade may be inputted using any device known in the art, e.g., keyboard, mouse, voice recognition, etc. The controller 210 compares the selected tooth shade input to the formula matrix stored in the memory 230. The controller 210 provides two or more dental restorative formulas correlated to the selected tooth shade input using the stored formula matrix. Each formula of the two or more dental restorative formulas includes at least one dental restorative composition code, and at least one formula of the two or more dental restorative formulas provided includes two or more dental restorative composition codes. The two or more dental restorative formulas may include a single composition formula, a two-composition formula, and/or a multi-composition formula as further described herein. The controller 210 displays the two or more dental restorative formulas on the display 220 for the practitioner. The practitioner may select at least one of the two or more dental restorative formulas provided on the display 220 to prepare a dental restorative to be applied to one or more of a patient's teeth.

Figure 7:
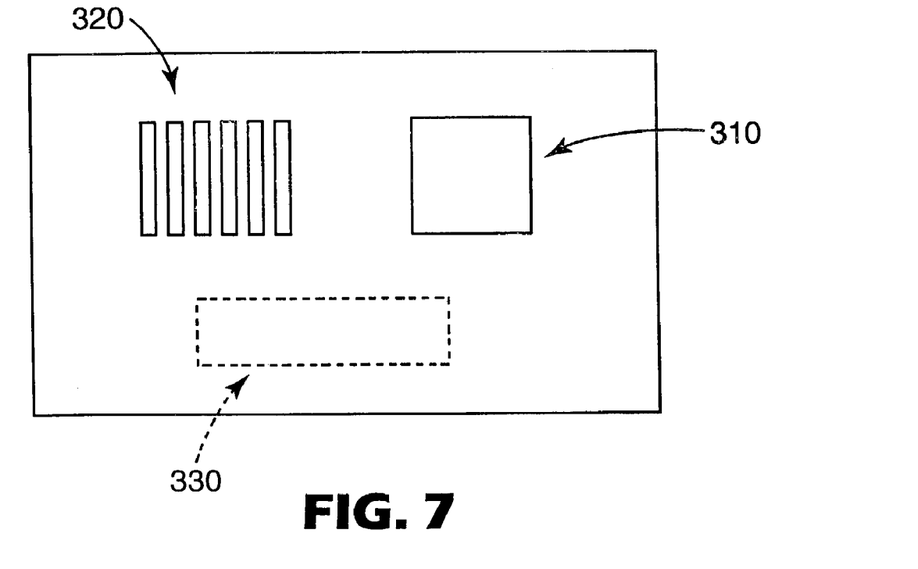
FIG. 7 is a schematic diagram of one embodiment of a dental restorative kit including a dental restorative formula selector according to the present invention.

Further, the dental restorative formula selectors of the present invention may be included in a dental restorative kit. FIG. 7 illustrates a dental restorative kit 300 according to one embodiment of the present invention. The kit 300 may include a dental restorative selector 310, e.g., dental restorative selector 100 of FIGS. 2–5, and at least one dental restorative composition 320 used to prepare dental restoratives. The kit may optionally include a tooth shade guide 330 as further described herein.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below.

What is claimed is:

1. A method of identifying a dental restorative formula, the method comprising:
    selecting a tooth shade;
    providing two or more dental restorative formulas correlated to the tooth shade, wherein each formula of the two or more dental restorative formulas comprises at least one dental restorative composition code, and further wherein at least one dental restorative formula of the two or more dental restorative formulas comprises at least two dental restorative composition codes; and
    selecting one dental restorative formula from the two or more dental restorative formulas as a selected dental restorative formula.

2. The method of claim 1, wherein the method further comprises restoring a tooth using the selected dental restorative formula.

3. The method of claim 2, wherein restoring the tooth comprises applying a dental restorative composition to the tooth using the selected dental restorative formula.

4. The method of claim 1, wherein selecting the tooth shade comprises:
    comparing a tooth to a shade guide, wherein the shade guide comprises a plurality of tooth shades; and
    matching the color of the tooth to one tooth shade of the plurality of tooth shades of the shade guide.

5. A method of identifying a dental restorative formula, the method comprising:
    selecting a tooth shade;
    providing a dental restorative formula selector comprising a formula matrix on a first major surface of a medium, wherein the formula matrix comprises:
        a plurality of tooth shade markings; and
        a plurality of dental restorative formulas, wherein two or more dental restorative formulas of the plurality of dental restorative formulas are correlated to each tooth shade marking of the plurality of tooth shade markings;
    providing two or more dental restorative formulas correlated to the tooth shade using the dental restorative formula selector, wherein each formula of the two or more dental restorative formulas comprises at least one dental restorative composition code, and further wherein at least one dental restorative formula of the two or more dental restorative formulas comprises at least two dental restorative composition codes; and
    selecting one dental restorative formula from the two or more dental restorative formulas as a selected dental restorative formula.

6. The method of claim 5, wherein selecting one dental restorative formula comprises:
    inputing the tooth shade into the dental restorative formula selector; and
    selecting one dental restorative formula from the two or more dental restorative formulas provided by the dental restorative formula selector.

7. The method of claim 5, wherein the two or more dental restorative formulas are selected from the group consisting of a single dental restorative composition formula, a two-composition dental restorative formula, and a multi-composition dental restorative formula.

8. A dental restorative formula selector computer system, the system comprising:
    a display;
    a memory device, wherein a formula matrix is stored in the memory device, wherein the formula matrix comprises a plurality of tooth shade markings and a plurality of dental restorative formulas, wherein two or more dental restorative formulas of the plurality of dental restorative formulas are correlated to each tooth shade marking of the plurality of tooth shade markings;
    a controller in communication with the memory device and the display, wherein the controller is operable to:
        receive a selected tooth shade input;
        compare the selected tooth shade input to the formula matrix stored in the memory;
        provide the two or more dental restorative formulas correlated to the selected tooth shade input using the formula matrix, wherein each dental restorative formula of the plurality of dental restorative formulas comprises at least one dental restorative composition code, and further wherein at least one dental restorative formula of the two or more dental restorative formulas correlated to each tooth shade marking comprises at least two dental restorative composition codes; and
        display the two or more dental restorative formulas on the display.

9. The system of claim 8, wherein at least one of the two or more dental restorative formulas correlated to each tooth shade marking comprises a single composition dental restorative formula.

10. The system of claim 8, wherein at least one of the two or more dental restorative formulas correlated to each tooth shade marking comprises a two-composition dental restorative formula.

11. The system of claim 8, wherein at least one of the two or more dental restorative formulas correlated to each tooth shade marking comprises a multi-composition dental restorative formula.

12. The system of claim 8, wherein the two or more dental restorative formulas provided by the controller comprise at least one of a single composition dental restorative formula and a two-composition dental restorative formula.

13. The system of claim 8, wherein the two or more dental restorative formulas provided by the controller comprise at least one of a single composition dental restorative formula and a multi-composition dental restorative formula.

14. The system of claim 8, wherein the two or more dental restorative formulas provided by the controller comprise at least one of a two-composition dental restorative formula and a multi-composition dental restorative formula.

15. The system of claim 8, wherein the two or more dental restorative formulas provided by the controller comprise a single composition dental restorative formula, a two-composition dental restorative formula, and a multi-composition dental restorative formula.

* * * * *

UNITED STATES PATENT AND TRADEMARK OFFICE
CERTIFICATE OF CORRECTION

PATENT NO.        : 6,971,874 B2
APPLICATION NO. : 10/272488
DATED             : December 6, 2005
INVENTOR(S)       : Fundingsland, Jon W.

Page 1 of 1

It is certified that error appears in the above-identified patent and that said Letters Patent is hereby corrected as shown below:

On Title page col. 2 Item (56) (U.S. Patent Documents) – Line 9 - After "2001/0049082" delete "A1" and insert --A2--, therfor.

Signed and Sealed this

Fifteenth Day of August, 2006

JON W. DUDAS
*Director of the United States Patent and Trademark Office*